United States Patent
Li et al.

(10) Patent No.: US 10,383,537 B2
(45) Date of Patent: Aug. 20, 2019

(54) PHYSIOLOGICAL SIGNAL MEASURING METHOD AND PHYSIOLOGICAL SIGNAL MEASURING DEVICE

(71) Applicant: INDUSTRIAL TECHNOLOGY RESEARCH INSTITUTE, Hsinchu (TW)

(72) Inventors: Szu-Ju Li, Changhua (TW); Pai-Hao Wu, New Taipei (TW); I-Cherng Chen, Hsinchu (TW); Hsin-Hung Pan, Luodong Township (TW); Jung-Hao Wang, New Taipei (TW); Ren-Der Jean, Hsinchu (TW); Meng-Song Yin, Hsinchu (TW); Chun-Te Chuang, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/680,407

(22) Filed: Aug. 18, 2017

(65) Prior Publication Data

US 2018/0168474 A1    Jun. 21, 2018

(30) Foreign Application Priority Data

Dec. 15, 2016   (TW) ................ 105141586

(51) Int. Cl.
*A61B 5/0408*   (2006.01)
*A61B 5/0205*   (2006.01)
(Continued)

(52) U.S. Cl.
CPC ........ *A61B 5/04085* (2013.01); *A61B 5/0205* (2013.01); *A61B 5/7225* (2013.01);
(Continued)

(58) Field of Classification Search
CPC ... A61B 5/0205; A61B 5/0809; A61B 5/0537; A61B 2562/0214; A61B 5/0245
See application file for complete search history.

(56) References Cited

U.S. PATENT DOCUMENTS

| | | | |
|---|---|---|---|
| 4,141,351 A | | 2/1979 | James et al. |
| 4,409,987 A | * | 10/1983 | McIntyre ........... A61B 5/04004 600/544 |

(Continued)

FOREIGN PATENT DOCUMENTS

| | | |
|---|---|---|
| CN | 104254275 A | 12/2014 |
| CN | 104602598 A | 5/2015 |

(Continued)

OTHER PUBLICATIONS

Baba A. et al., "Electrical Characterisation of Dry Electrodes for ECG Recording", 12th WSEAS International Conference on Circuits, Heraklion, Greece, Jul. 22-24, 2008, pp. 76-81.

(Continued)

*Primary Examiner* — Sean P Dougherty
(74) *Attorney, Agent, or Firm* — Birch, Stewart, Kolasch & Birch, LLP (57) ABSTRACT

A physiological signal measuring method and a physiological signal measuring device are provided. The physiological signal measuring method includes the following steps: A first inputting signal having a first frequency, a second inputting signal having a second frequency and a third inputting signal having a third frequency are respectively inputted to at least two electrode sheets attached on a skin. A first impedance value corresponding to the first inputting signal, a second impedance value corresponding to the second inputting signal and a third impedance value corresponding to the third inputting signal are respectively measured. An interference impedance between the electrode sheets and the skin is obtained according to the first fre- (Continued)

quency, the second frequency, the third frequency, the first impedance value, the second impedance value and the third impedance value. A measured physiological signal is corrected according to the interference impedance to obtain a corrected physiological signal.

16 Claims, 6 Drawing Sheets

(51) Int. Cl.
  *A61B 5/00* (2006.01)
  *A61B 5/0245* (2006.01)
  *A61B 5/053* (2006.01)
  *A61B 5/08* (2006.01)
(52) U.S. Cl.
  CPC ............ *A61B 5/0245* (2013.01); *A61B 5/053* (2013.01); *A61B 5/0537* (2013.01); *A61B 5/0809* (2013.01); *A61B 2562/0214* (2013.01); *A61B 2562/046* (2013.01)

(56) References Cited

U.S. PATENT DOCUMENTS

| | | | | |
|---|---|---|---|---|
| 5,704,365 | A * | 1/1998 | Albrecht | A61B 5/0408 128/901 |
| 5,792,063 | A * | 8/1998 | Danielsson | A61B 5/0424 600/509 |
| 5,978,693 | A | 11/1999 | Hamilton et al. | |
| 6,339,722 | B1 * | 1/2002 | Heethaar | A61B 5/0535 600/547 |
| 6,496,721 | B1 * | 12/2002 | Yonce | A61B 5/0428 600/509 |
| 6,577,893 | B1 | 6/2003 | Besson et al. | |
| 6,625,487 | B2 | 9/2003 | Herleikson | |
| 6,643,540 | B2 | 11/2003 | Yonce | |
| 6,912,414 | B2 | 6/2005 | Tong | |
| 6,974,420 | B2 | 12/2005 | Kaiser et al. | |
| 7,340,294 | B2 | 3/2008 | Gray | |
| 7,818,058 | B2 | 10/2010 | Mentelos | |
| 8,412,317 | B2 | 4/2013 | Mazar | |
| 8,868,205 | B2 | 10/2014 | Ross et al. | |
| 9,131,915 | B2 | 9/2015 | Amiri Farahani et al. | |
| 9,603,521 | B2 * | 3/2017 | Cho | A61B 5/00 |
| 9,955,916 | B2 * | 5/2018 | Bonomi | A61B 5/0537 |
| 10,022,064 | B2 * | 7/2018 | Kim | A61B 5/053 |
| 2002/0077534 | A1 * | 6/2002 | DuRousseau | G06F 3/015 600/300 |
| 2003/0135129 | A1 * | 7/2003 | Cusimano | A61B 5/0488 600/546 |
| 2004/0092801 | A1 * | 5/2004 | Drakulic | A61B 5/04 600/300 |
| 2004/0122336 | A1 * | 6/2004 | Jang | A61B 5/0531 600/547 |
| 2004/0181164 | A1 * | 9/2004 | Smith | A61B 5/053 600/547 |
| 2005/0203431 | A1 * | 9/2005 | Brodnick | A61B 5/0809 600/529 |
| 2006/0178706 | A1 * | 8/2006 | Lisogurski | A61B 5/04028 607/10 |
| 2007/0129759 | A1 | 6/2007 | Colthurst | |
| 2007/0135727 | A1 * | 6/2007 | Virtanen | A61B 5/04004 600/544 |
| 2007/0142735 | A1 * | 6/2007 | Shin | A61B 5/0424 600/509 |
| 2007/0167858 | A1 * | 7/2007 | Virtanen | A61B 5/04004 600/544 |
| 2008/0009759 | A1 * | 1/2008 | Chetham | A61B 5/02028 600/526 |
| 2008/0275316 | A1 * | 11/2008 | Fink | A61B 5/04004 600/306 |
| 2008/0319336 | A1 * | 12/2008 | Ward | A61B 5/0537 600/547 |
| 2009/0043222 | A1 * | 2/2009 | Chetham | A61B 5/0537 600/547 |
| 2009/0076340 | A1 * | 3/2009 | Libbus | A61B 5/0006 600/301 |
| 2009/0082829 | A1 * | 3/2009 | Panken | A61N 1/36139 607/45 |
| 2009/0143663 | A1 * | 6/2009 | Chetham | A61B 5/053 600/372 |
| 2010/0113898 | A1 * | 5/2010 | Kim | A61B 5/0261 600/310 |
| 2010/0268110 | A1 | 10/2010 | Beltrán et al. | |
| 2011/0264000 | A1 * | 10/2011 | Paul | A61B 5/0537 600/547 |
| 2011/0301489 | A1 * | 12/2011 | Essex | A61B 5/0531 600/547 |
| 2012/0116741 | A1 | 5/2012 | Choi et al. | |
| 2012/0165622 | A1 | 6/2012 | Rodríguez Ibáñez et al. | |
| 2012/0232369 | A1 * | 9/2012 | Kim | A61B 5/0428 600/372 |
| 2012/0330167 | A1 * | 12/2012 | Gaw | A61B 5/0537 600/481 |
| 2013/0197340 | A1 * | 8/2013 | Sanders | A61B 5/02007 600/384 |
| 2014/0187974 | A1 | 7/2014 | Banet et al. | |
| 2014/0187995 | A1 * | 7/2014 | Hu | A61B 5/0492 600/546 |
| 2014/0247058 | A1 | 9/2014 | Mortara | |
| 2015/0201861 | A1 * | 7/2015 | Ko | A61B 5/053 600/547 |
| 2015/0327815 | A1 * | 11/2015 | Hwang | A61B 5/053 600/547 |
| 2015/0351690 | A1 * | 12/2015 | Toth | A61B 5/6833 600/373 |
| 2015/0359491 | A1 * | 12/2015 | Luna | A61B 5/7246 600/301 |
| 2016/0007878 | A1 * | 1/2016 | Leuthardt | A61B 5/721 600/301 |
| 2016/0015352 | A1 * | 1/2016 | Brown | A61B 6/541 600/413 |
| 2016/0055415 | A1 | 2/2016 | Baxi | |
| 2016/0135741 | A1 * | 5/2016 | Chetham | A61B 5/0537 600/391 |
| 2016/0274726 | A1 * | 9/2016 | Chung | G06F 3/014 |
| 2016/0367186 | A1 * | 12/2016 | Freeman | A61B 5/0022 |
| 2018/0028809 | A1 * | 2/2018 | Ziv | A61H 39/002 |
| 2018/0235499 | A1 * | 8/2018 | Zorman | A61B 5/0408 |
| 2018/0333056 | A1 * | 11/2018 | Chou | A61B 5/0205 |

FOREIGN PATENT DOCUMENTS

| | | |
|---|---|---|
| CN | 103037763 B | 3/2016 |
| CN | 105748072 A | 7/2016 |
| JP | 5855534 B2 | 2/2016 |
| TW | 179982 | 3/1992 |
| TW | 517577 | 1/2003 |
| TW | 531405 | 5/2003 |
| TW | 201316950 A1 | 5/2013 |
| TW | I410233 B | 10/2013 |
| TW | I421509 B | 1/2014 |
| TW | I450707 B | 9/2014 |
| TW | I482612 B | 5/2015 |
| TW | I493213 B | 7/2015 |
| TW | I505811 B | 11/2015 |
| TW | 201545718 A | 12/2015 |
| TW | I533840 B | 5/2016 |
| TW | I535420 B | 6/2016 |

OTHER PUBLICATIONS

Dozio et al., "Time Based Measurement of the Impedance of the Skin-Electrode Interface for Dry Electrode ECG Recording", Proceedings of the 29th Annual International Conference of the IEEE EMBS, Cite Internationale, Lyon, France, Aug. 23-26, 2007, pp. 5001-5004.

Taiwanese Office Action issued by TIPO for Application No. 105141586, dated Feb. 14, 2017.

(56) References Cited

OTHER PUBLICATIONS

Taji et al., "Impact of Skin-Electrode Interface on Electrocardiogram Measurements Using Conductive Textile Electrodes", IEEE Transactions on Instrumentation and Measurement, Jun. 2014, vol. 63, No. 6, pp. 1412-1422.

Tomczyk, "Procedure for Correction of the ECG Signal Error Introduced by Skin-Electrode Interface", Metrol. Meas. Syst., 2011, vol. XVIII, No. 3, pp. 461-470.

* cited by examiner

PHYSIOLOGICAL SIGNAL MEASURING METHOD AND PHYSIOLOGICAL SIGNAL MEASURING DEVICE

This application claims the benefit of Taiwan application Serial No. 105141586, filed Dec. 15, 2016, the disclosure of which is incorporated by reference herein in its entirety.

TECHNICAL FIELD

The disclosure relates in general to a physiological signal measuring method and a physiological signal measuring device.

BACKGROUND

Along with the advance and development in technology, a physiological signal measuring device is provided. The physiological signal measuring device can measure relevant health information of a person-under-test, such as the respiratory rate and the heart rate. As people's awareness of health keeps growing, the physiological signal measuring device has been widely used in various medical institutions and households. However, the accuracy and stability of the physiological signal measuring device is susceptible to the contact state between the electrode sheets and the skin. Particularly, interference will become even worse when fabric electrodes are used or when the person-under-test makes a large movement.

SUMMARY

The disclosure is directed to a physiological signal measuring method and a physiological signal measuring device.

According to one embodiment of the disclosure, a physiological signal measuring method is provided. The physiological signal measuring method includes the following steps: A first inputting signal having a first frequency, a second inputting signal having a second frequency and a third inputting signal having a third frequency are respectively inputted to at least two electrode sheets attached on a skin. A first impedance value corresponding to the first inputting signal, a second impedance value corresponding to the second inputting signal and a third impedance value corresponding to the third inputting signal between the electrode sheets and the skin are respectively measured. An interference impedance between the electrode sheets and the skin is obtained according to the first frequency, the second frequency, the third frequency, the first impedance value, the second impedance value and the third impedance value. The skin is measured to obtain a measured physiological signal. The measured physiological signal is corrected according to the interference impedance to obtain a corrected physiological signal.

According to another embodiment of the disclosure, a physiological signal measuring device is provided. The physiological signal measuring device includes at least two electrode sheets, a signal inputting unit, an impedance measuring unit, a computing unit, a physiological signal measuring unit and a signal processing unit. The electrode sheets are attached on a skin. The signal inputting unit respectively inputs a first inputting signal having a first frequency, a second inputting signal having a second frequency and a third inputting signal having a third frequency to at least two electrode sheets attached on a skin. The impedance measuring unit respectively measures a first impedance value corresponding to the first inputting signal, a second impedance value corresponding to the second inputting signal and a third impedance value corresponding to the third inputting signal between the electrode sheets and the skin. The computing unit obtains an interference impedance between the electrode sheets and the skin according to the first frequency, the second frequency, the third frequency, the first impedance value, the second impedance value and the third impedance value. The physiological signal measuring unit measures the skin to obtain a measured physiological signal. The signal processing unit corrects the measured physiological signal according to the interference impedance to obtain a corrected physiological signal.

The above and other aspects of the disclosure will become better understood with regard to the following detailed description of the preferred but non-limiting embodiment(s). The following description is made with reference to the accompanying drawings.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 1:
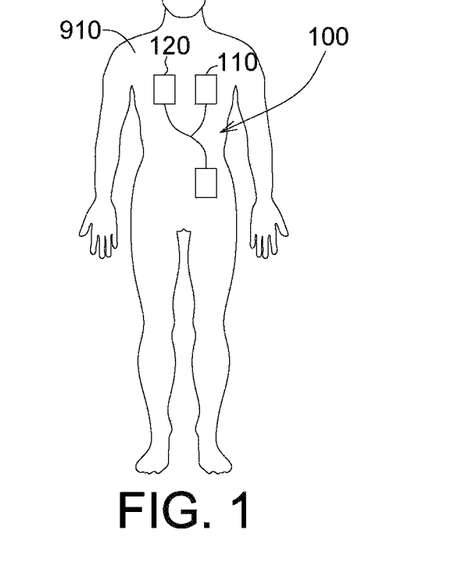
FIG. 1 is a schematic diagram of a physiological signal measuring device.

Referring to FIG. 1, a schematic diagram of a physiological signal measuring device 100 is shown. The physiological signal measuring device 100 can measure a person-under-test's physiological signals, such as respiratory signals, heart rate signals or body fat rate signals by using at least two electrode sheets 110 and 120. During the measuring process, the electrode sheets 110 and 120 are attached on the person-under-test's skin 910. However, during the measuring process, an interface interference may be generated between the electrode sheets 110 and 120 and the skin 910 and affect the accuracy and stability of measurement.

Figure 2:
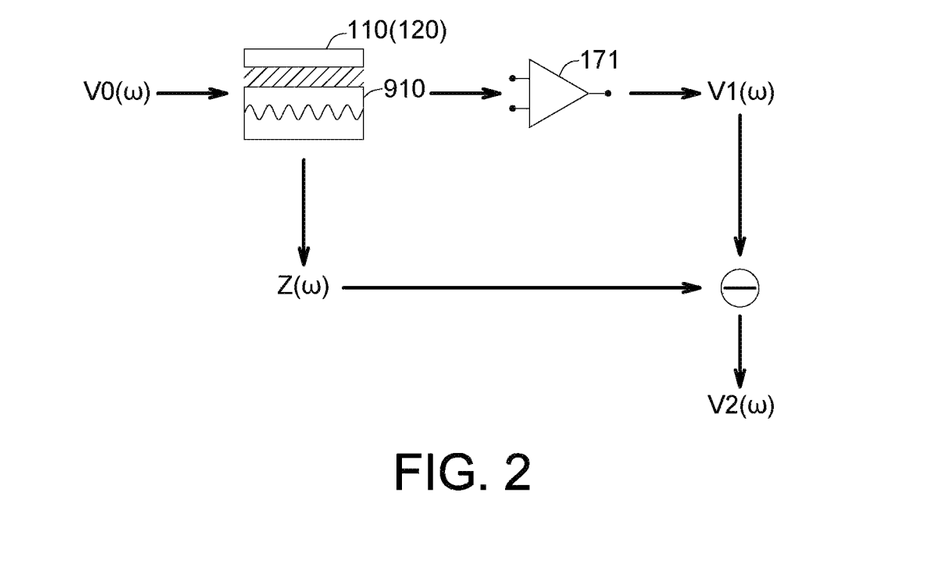
FIG. 2 is a circuit diagram of interference impedance according to an embodiment.

Referring to FIG. 2, a circuit diagram of interference impedance $Z(\omega)$ according to an embodiment is shown. After a body physiological signal $V0(\omega)$ is transmitted to an amplifier 171 through the electrode sheets 110 and 120 and the skin 910, a measured physiological signal $V1(\omega)$ that has been affected by the interface interference between the electrode sheets 110 and 120 and the skin 910 is measured, wherein ω denotes frequency. The physiological signal measuring device of the present embodiment can estimate an interference impedance $Z(\omega)$ by using an analysis processing procedure and then correct the measured physiological signal $V1(\omega)$ according to the interference impedance $Z(\omega)$ to obtain a corrected physiological signal $V2(\omega)$. Since the corrected physiological signal $V2(\omega)$ is close to the actual body physiological signal $V0(\omega)$, the accuracy and stability of measurement is greatly enhanced.

The interference impedance $Z(\omega)$ is a function of frequency. If the signals of all frequency are inputted point by point, the value of interference impedance $Z(\omega)$ can be measured point by point and the curve of interference impedance $Z(\omega)$ can be constructed through curve fitting. However, such practice is very time-consuming and can only be done in an off-line manner. It cannot be done on a wearable device. Here below, a fast analytic method capable of solving the function of interference impedance $Z(\omega)$ can be obtained through the input of three inputting signals corresponding to three frequencies.

Figure 3:
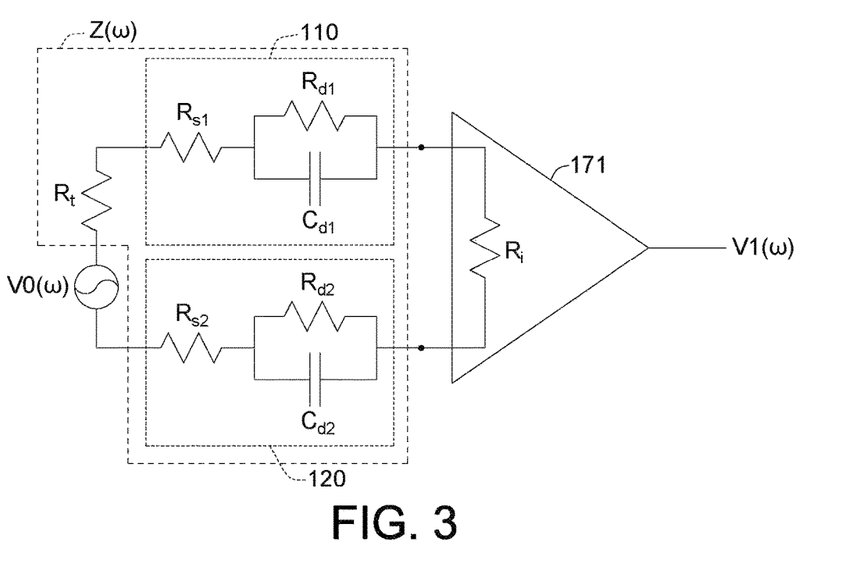
FIG. 3 is an equivalent circuit model diagram of interference impedance.

Referring to FIG. 3, an equivalent circuit model diagram of interference impedance $Z(\omega)$ is shown. The interference impedance $Z(\omega)$ is generated between the body physiological signal $V0(\omega)$ and the amplifier 171 having an impedance of $R_i$. The relationship between the body physiological signal $V0(\omega)$ and the measured physiological signal $V1(\omega)$ can be expressed as formula (1):

$$V0(\omega) = V1(\omega) \times \frac{R_i + Z(\omega)}{R_i} \qquad (1)$$

Therefore, based on formula (1), the body physiological signal $V0(\omega)$ can be obtained if the interference impedance $Z(\omega)$ is known.

As indicated in FIG. 3, the interference impedance $Z(\omega)$ includes equivalent resistance $R_t$ of skin tissue, equivalent resistances $R_{s1}$ and $R_{s2}$ of conductive adhesive and sweat, equivalent resistances $R_{d1}$ and $R_{d2}$ of the charge transfer between the electrode sheets 110 and 120 and the skin, and equivalent capacitances $C_{d1}$ and $C_{d2}$ between the electrode sheets 110 and 120 and the skin.

Generally speaking, the two electrode sheets 110 and 120 mostly are selected from the same production and the same model, such that measurement error can be reduced. Given that the electrode sheets 110 and 120 are identical, the equivalent circuit model of FIG. 3 can be simplified to the equivalent circuit model of FIG. 4. In another embodiment, the physiological signal measuring device 100 may include at least two electrode sheets, that is, the physiological signal $V0(\omega)$ is measured through at least two electrode sheets. Under such circumstance, any two electrode sheets can be for measuring the interference impedance $Z(\omega)$, but the disclosure is not limited thereto. The interference impedance $Z(\omega)$ of FIG. 4 includes equivalent resistance $R_s$ of conductive adhesive and sweat, equivalent resistance $R_d$ of the charge transfer between the electrode sheets 110 and 120 and the skin, and equivalent capacitance $C_d$ between the electrode sheets 110 and 120 and the skin, wherein, $R_{S1}=R_{S2}=R_S$, $R_{d1}=R_{d2}=R_d$, $C_{d1}=C_{d2}=C_d$. The equivalent resistance $R_t$ of skin tissue can be included in the equivalent resistance $R_s$.

Figure 4:
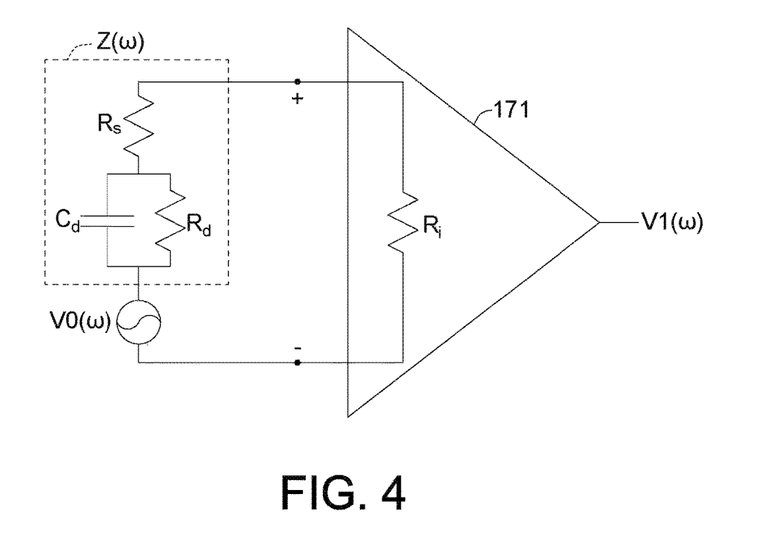
FIG. 4 is a simplified equivalent circuit model of interference impedance.

The relationship between the interference impedance $Z(\omega)$, the equivalence resistances $R_d$, $R_s$ and the equivalent capacitances $C_d$ can be expressed as formula (2):

$$Z(\omega) = R_s + \frac{R_d}{1 + j\omega C_d R_d} \qquad (2)$$

The real parts of interference impedance $Z(\omega)$ is $\mathrm{Re}(Z(\omega))$ which can be expressed as formula (3):

$$\mathrm{Re}(Z(\omega)) = R_s + \frac{R_d}{1 + \omega^2 C_d^2 R_d^2} \qquad (3)$$

Let $R_d$ be y, and $C_d^2 R_d^2$ be x, then $\mathrm{Re}(Z(\omega))$ can be simplified as formula (4):

$$\mathrm{Re}(Z(\omega)) = R_s + \frac{y}{1 + \omega^2 x} \qquad (4)$$

Figure 5:
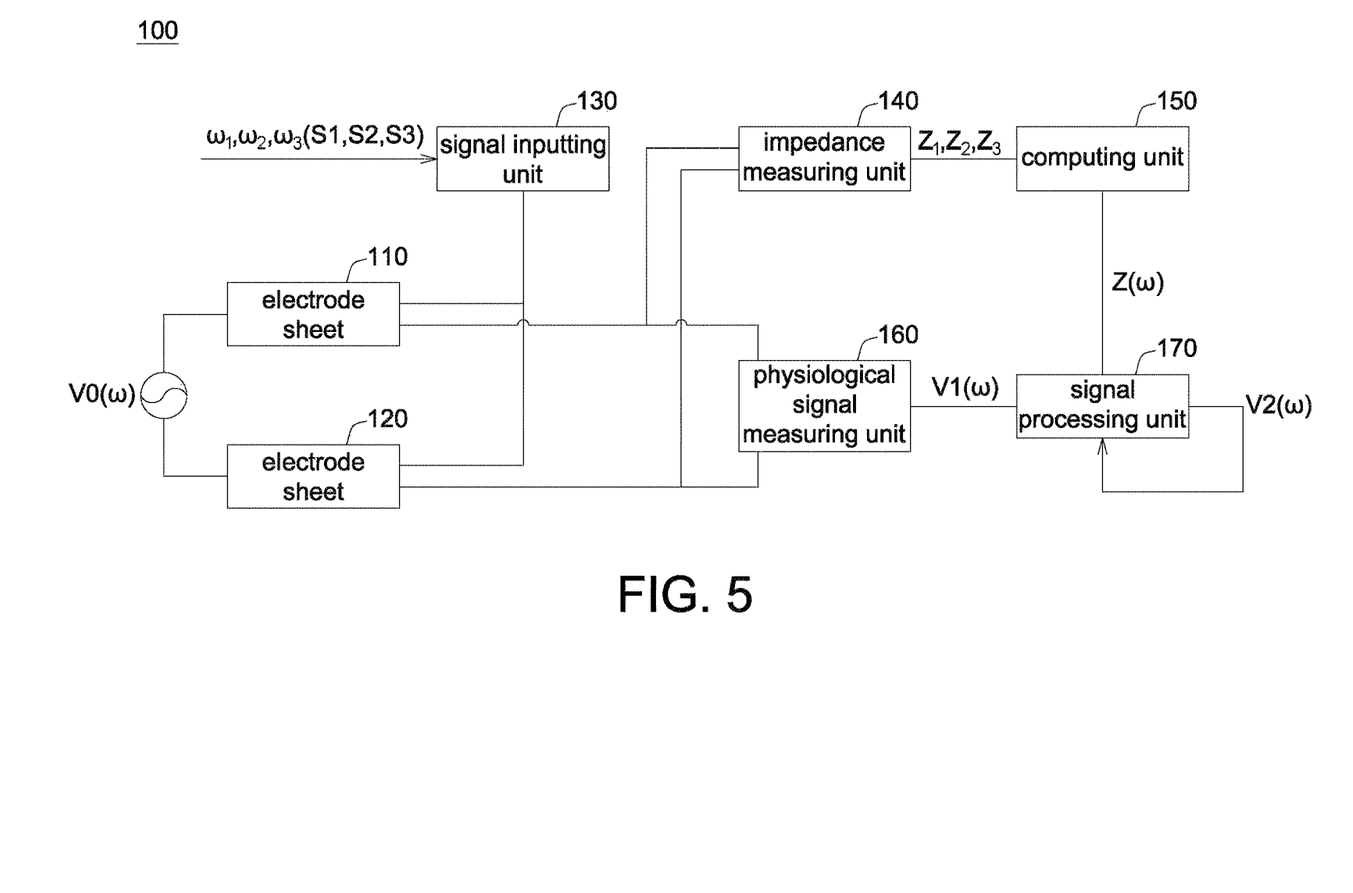
FIG. 5 is a block diagram of a physiological signal measuring device according to an embodiment.

A first inputting signal S1 having a first frequency $\omega_1$ (illustrated in FIG. 5), a second inputting signal S2 having a second frequency $\omega_2$ (illustrated in FIG. 5) and a third inputting signal S3 having a third frequency $\omega_3$ (illustrated in FIG. 5) are respectively inputted to the at least two electrode sheets, such that a first impedance value $Z_1$, a second impedance value $Z_2$, and a third impedance value $Z_3$ are respectively measured. The first impedance value $Z_1$, the second impedance value $Z_2$ and the third impedance value $Z_3$ can be expressed as formula (5):

$$\begin{cases} Z_1 = R_s + \dfrac{y}{1 + \omega_1^2 x} \\ Z_2 = R_s + \dfrac{y}{1 + \omega_2^2 x} \\ Z_3 = R_s + \dfrac{y}{1 + \omega_3^2 x} \end{cases} \qquad (5)$$

Let $A_1$ be the second impedance value $Z_2$ deducted by the first impedance value $Z_1$, and $A_2$ be the third impedance value $Z_3$ deducted by the first impedance value $Z_1$, then $A_1$ and $A_2$ can be expressed as formula (6):

$$\begin{cases} A_1 = Z_2 - Z_1 = \dfrac{y}{1+\omega_2^2 x} - \dfrac{y}{1+\omega_1^2 x} \\ A_2 = Z_3 - Z_1 = \dfrac{y}{1+\omega_3^2 x} - \dfrac{y}{1+\omega_1^2 x} \end{cases} \qquad (6)$$

Based on formula (6), y can be expressed as formulae (7) and (8):

$$y = \frac{A_1(\omega_1^2 \omega_2^2 x^2 + (\omega_1^2 + \omega_2^2)x + 1)}{x(\omega_1^2 - \omega_2^2)} \qquad (7)$$

$$= \frac{A_1 \omega_1^2 \omega_2^2}{\omega_1^2 - \omega_2^2} x + \frac{A_1(\omega_1^2 + \omega_2^2)}{\omega_1^2 - \omega_2^2} + \frac{A_1}{\omega_1^2 - \omega_2^2} \frac{1}{x}$$

$$y = \frac{A_2(\omega_1^2 \omega_3^2 x^2 + (\omega_1^2 + \omega_3^2)x + 1)}{x(\omega_1^2 - \omega_3^2)} \qquad (8)$$

$$= \frac{A_2 \omega_1^2 \omega_3^2}{\omega_1^2 - \omega_3^2} x + \frac{A_2(\omega_1^2 + \omega_3^2)}{\omega_1^2 - \omega_3^2} + \frac{A_2}{\omega_1^2 - \omega_3^2} \frac{1}{x}$$

Let $a_1$ be $$\frac{A_1\omega_1^2\omega_2^2}{\omega_1^2-\omega_2^2},$$

$b_1$ be $$\frac{A_1(\omega_1^2+\omega_2^2)}{\omega_1^2-\omega_2^2},$$

$c_1$ be $$\frac{A_1}{\omega_1^2-\omega_2^2},$$

$a_2$ be $$\frac{A_2\omega_1^2\omega_3^2}{\omega_1^2-\omega_3^2},$$

$b_2$ be $$\frac{A_2(\omega_1^2+\omega_3^2)}{\omega_1^2-\omega_3^2},$$

and $c_2$ be $$\frac{A_2}{\omega_1^2-\omega_3^2},$$

then y can be expressed as formula (9):

$$\begin{cases} y = a_1 x + b_1 + c_1 \frac{1}{x} \\ y = a_2 x + b_2 + c_2 \frac{1}{x} \end{cases} \quad (9)$$

A new formula formed by deducting the second equation from the first equation of formula (9) can be expressed as formula (10):

$$(a_1-a_2)x^2+(b_1-b_2)x+(c_1-c_2)=0 \quad (10)$$

The solution to x of formula (10) of can be expressed as (11):

$$x = \frac{-(b_1-b_2) \pm \sqrt{(b_1-b_2)^2 - 4(a_1-a_2)(c_1-c_2)}}{2(a_1-a_2)} \quad (11)$$

Based on formula (9) and the definition of y, the equivalent resistance $R_d$ can be expressed as formula (12):

$$R_d = a_1 x + b_1 + c_1 \frac{1}{x} \quad (12)$$

Wherein, x of formula (12) can be substituted by x as defined in formula (11).

Based on the definition of x, equivalent capacitance $C_d$ can be expressed as formula (13):

$$C_d = \frac{\sqrt{x}}{R_d} \quad (13)$$

Wherein, x of formula (13) can be substituted by x as defined in formula (11).

Based on formula (3), equivalent resistance $R_s$ can be expressed as formula (14):

$$R_s = Z - \frac{R_d}{1 + \omega^2 C_d^2 R_d^2} \quad (14)$$

In the formulae (12) to (14) of equivalent resistances $R_d$, $R_s$ and equivalent capacitance $C_d$, the parameters $a_1$, $b_1$, $c_1$, $a_2$, $b_2$, $c_2$ can be obtained according to the first frequency $\omega_1$, the second frequency $\omega_1$, the third frequency $\omega_3$, the first impedance value $Z_1$, the second impedance value $Z_1$, and the third impedance value $Z_3$. Therefore, once the first frequency $\omega_1$, the second frequency $\omega_1$, the third frequency $\omega_3$, the first impedance value $Z_1$, the second impedance value $Z_1$, and the third impedance value $Z_3$ are obtained, the equivalent resistances $R_d$, $R_s$ and the equivalent capacitance $C_d$ will be obtained accordingly. Then, based on formula (2), the interference impedance $Z(\omega)$ can also be obtained. Furthermore, based on the above formulas, the equivalent resistances $R_d$, $R_s$ and the equivalent capacitance $C_d$ can be obtained according to the imaginary parts of interference impedance $Z(\omega)$, and the interference impedance $Z(\omega)$ can be obtained by the same analogy. However, details of deduction are not described here.

Referring to FIG. 5, a block diagram of a physiological signal measuring device 100 according to an embodiment is shown. The physiological signal measuring device 100 includes the said two electrode sheets 110 and 120, a signal inputting unit 130, an impedance measuring unit 140, a computing unit 150, a physiological signal measuring unit 160 and a signal processing unit 170. The electrode sheets 110 and 120 are attached on the skin 910 (illustrated in FIG. 1), wherein each of the electrode sheets 110 and 120 can be realized by such as a soft conductive patch, a fabric electrode, a metal pad, or a metal grip. Each of the signal inputting unit 130, the impedance measuring unit 140 and the physiological signal measuring unit 160 can be realized by such as a circuit, a chip or a circuit board. In the present embodiment, the impedance measuring unit 140 and the physiological signal measuring unit 160 share the same set of electrode sheets 110 and 120. Each of the computing unit 150 and the signal processing unit 170 can be realized by such as a circuit, a chip, a circuit board or a recording device storing multiple sets of programming codes. The operation of each element disclosed above is described below with an accompanying flowchart.

Figure 6:
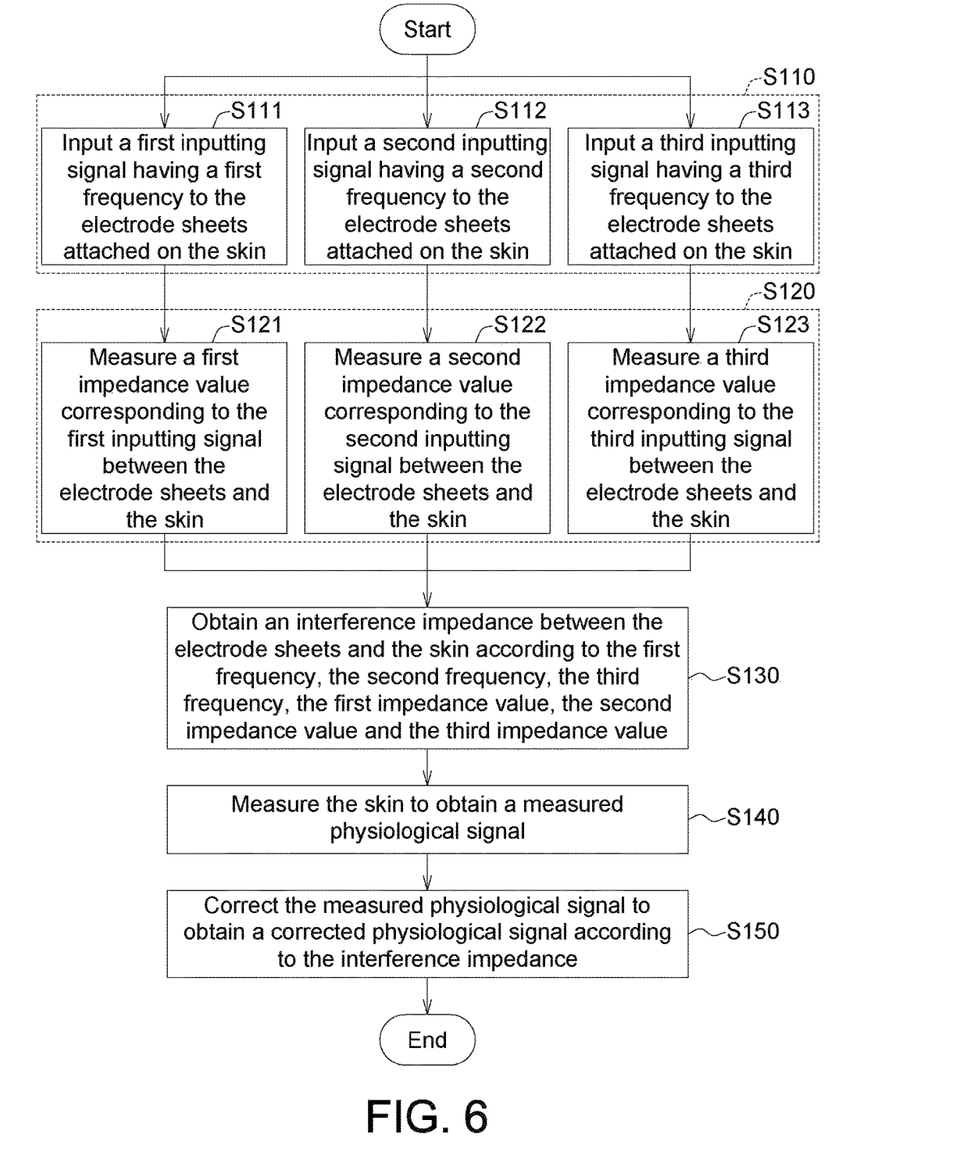
FIG. 6 is a flowchart of a physiological signal measuring method according to an embodiment.

Referring to FIG. 6, a flowchart of a physiological signal measuring method according to an embodiment is shown. In step S110, a first inputting signal S1 having a first frequency $\omega_1$, a second inputting signal S2 having a second frequency $\omega_2$ and a third inputting signal S3 having a third frequency $\omega_3$ are respectively inputted to one of the two electrode sheets 110 and 120 by the signal inputting unit 130 (steps S111, S112 and S113), wherein the two electrode sheets 110 or 120 are attached on a skin. In an embodiment, the first frequency $\omega_1$ is smaller than 0.5 Hz, the third frequency $\omega_3$ ranges from 150 Hz to 200 Hz, and the second frequency $\omega_2$ is an average of the first frequency $\omega_1$ and the third frequency $\omega_3$.

In an embodiment, each of the first inputting signal S1, the second inputting signal S2 and the third inputting signal S3 can be an AC electric signal. In another embodiment, the first inputting signal S1 having a lower frequency can be a DC electric signal.

In step S120, a first impedance value $Z_1$ corresponding to the first inputting signal S1, a second impedance value $Z_2$ corresponding to the second inputting signal S2 and a third impedance value $Z_3$ corresponding to the third inputting signal S3 between the electrode sheets 110 and 120 and the skin 910 are respectively measured by the impedance measuring unit 140 (steps S121, S122 and S123).

In an embodiment, firstly, the step S111 of inputting the first inputting signal S1 and the step S121 of measuring the first impedance value $Z_1$ are performed; then, the step S112 of inputting the second inputting signal S2 and the step S122 of measuring the second impedance value $Z_2$ are performed; lastly, the step S113 of inputting the third inputting signal S3 and the step S123 of measuring the third impedance value $Z_3$ are performed. It should be noted that in step S110 of the inputting signals and step S120 of measuring the impedance values, it does not matter which of the first inputting signal S1, the second inputting signal S2 and the third inputting signal S3 is processed first. What really matters is that after an inputting signal having a frequency is inputted to the signal inputting unit 130, the impedance value corresponding to the inputting signal having the frequency is measured prior to input another inputting signal.

Then, the method proceeds to step S130, the interference impedance $Z(\omega)$ between the electrode sheets 110 and 120 and the skin 910 is obtained by the computing unit 150 according to the first frequency $\omega_1$, the second frequency $\omega_2$, the third frequency $\omega_3$, the first impedance value $Z_1$, the second impedance value $Z_2$, the third impedance value $Z_3$.

Then, the method proceeds to step S140, the skin 910 is measured by the physiological signal measuring unit 160 to obtain a measured physiological signal $V1(\omega)$.

Then, the method proceeds to step S150, the measured physiological signal $V1(\omega)$ is corrected by the signal processing unit 170 according to the interference impedance $Z(\omega)$ to obtain a corrected physiological signal $V2(\omega)$. Then, the signal processing unit 170 can perform inverse Fourier transform on the corrected physiological signal $V2(\omega)$ to obtain a time domain waveform of the signal.

In an embodiment, step S110 to step S150 can be repeatedly performed. That is, after step S110 to step S150 are performed in sequence, step S110 is performed to update the interference impedance $Z(\omega)$ and correct the measured physiological signal $V1(\omega)$. In another embodiment, after step S110 to step S150 are performed in sequence, step S140 and step S150 are performed to correct the measured physiological signal $V1(\omega)$. Meanwhile, the interference impedance $Z(\omega)$ most recently calculated is corrected. After a period of time, the method returns to step S110 to update the interference impedance $Z(\omega)$.

In an embodiment, the impedance measuring unit 140 and the physiological signal measuring unit 160 can be directly connected to the electrode sheets 110, such that the step S120 of measuring the first impedance value $Z_1$, the second impedance value $Z_2$ and the third impedance value $Z_3$ and the step S140 of measuring the measured physiological signal $V1(\omega)$ can be performed concurrently.

Figure 7:
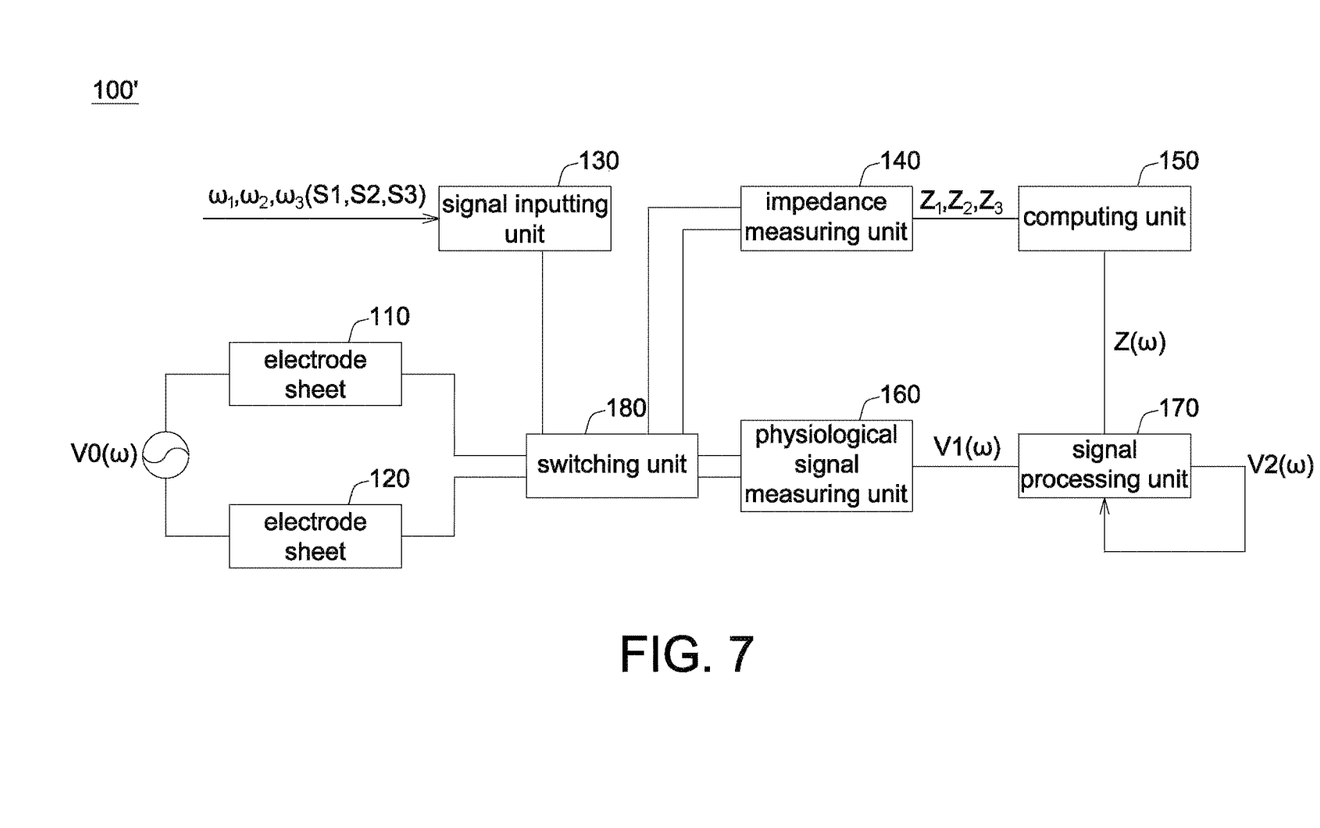
FIG. 7 is a block diagram of a physiological signal measuring device according to another embodiment.

Referring to FIG. 7, a block diagram of a physiological signal measuring device 100' according to another embodiment is shown. In another embodiment, the physiological signal measuring device 100' may further include a switching unit 180. The switching unit 180 can switch the electrode sheets 110 and 120 to be electrically connected to the impedance measuring unit 140 or the physiological signal measuring unit 160, such that the step S120 of measuring the first impedance value $Z_1$, the second impedance value $Z_2$, the third impedance value $Z_3$ and the step S140 of measuring the measured physiological signal $V1(\omega)$ can be performed separately.

Figure 8:
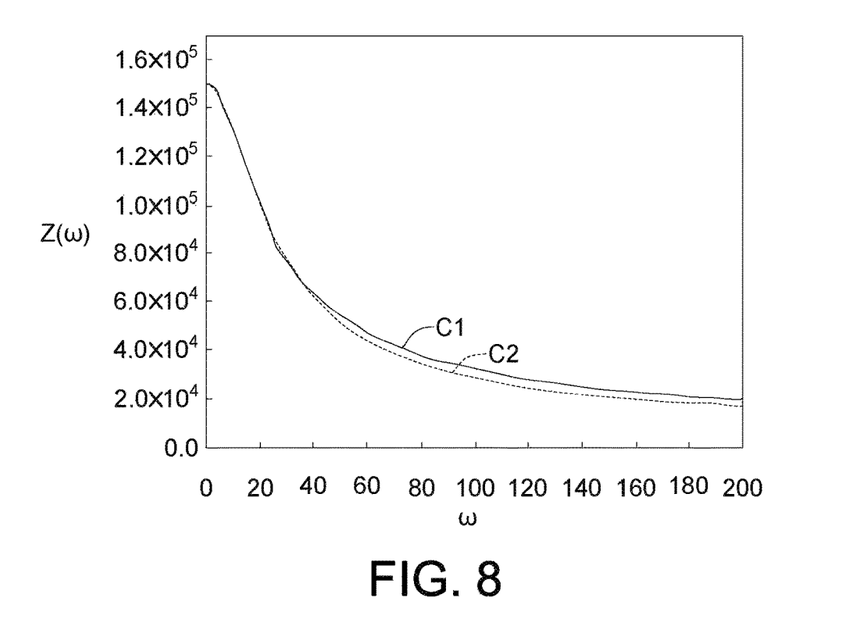
FIG. 8 is a result of interference impedance obtained by using a fast analytic method of the present embodiment.

Referring to FIG. 8, a result of an interference impedance $Z(\omega)$ obtained by using a fast analytic method of the present embodiment is shown. Curve C1 presents the interference impedance $Z(\omega)$ measured by an instrument, and curve C2 presents the interference impedance $Z(\omega)$ obtained by using the fast analytic method of the present embodiment. A comparison between curve C1 and curve C2 shows that the discrepancy between curve C1 and curve C2 is less than 5%, which indicates that the measurement has high accuracy.

Figure 9:
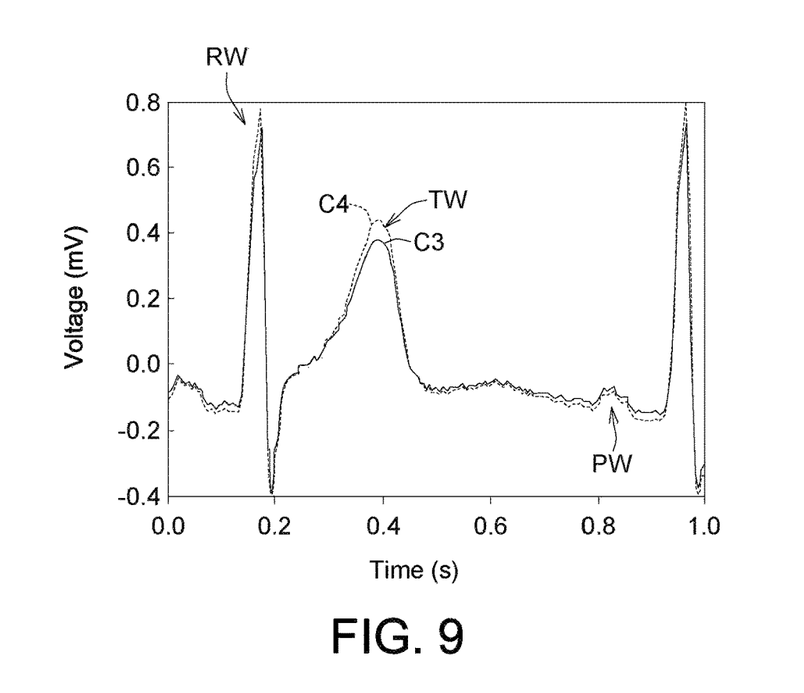
FIG. 9 is a result of an ECG signal without interference impedance.

Referring to FIG. 9, a result of an ECG signal without interference impedance $Z(\omega)$ is shown. The ECG signal with interference impedance $Z(\omega)$ is denoted by curve C3. The ECG signal without interference impedance $Z(\omega)$ is denoted by curve C4. A comparison between curve C3 and curve C4 shows that curve C4 has a 13% increase in R-wave RW, a 15% increase in T-wave TW, and an 18% in P-wave PW. Thus, the intensity of the physiological signal is effectively enhanced, and the accuracy of data processing is increased.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A physiological signal measuring method, comprising:
respectively inputting a first inputting signal having a first frequency, a second inputting signal having a second frequency and a third inputting signal having a third frequency to at least two electrode sheets attached on a skin;
respectively measuring a first impedance value corresponding to the first inputting signal, a second impedance value corresponding to the second inputting signal and a third impedance value corresponding to the third inputting signal between the electrode sheets and the skin, and;
obtaining an interference impedance between the electrode sheets and the skin according to the first frequency, the second frequency, the third frequency, the first impedance value, the second impedance value and the third impedance value;
measuring the skin to obtain a measured physiological signal; and
correcting the measured physiological signal to obtain a corrected physiological signal according to the interference impedance.

2. The physiological signal measuring method according to claim 1, wherein the first frequency, the second frequency and the third frequency are different from each other.

3. The physiological signal measuring method according to claim 1, wherein the first frequency is smaller than 0.5 Hz, the third frequency ranges from 150 Hz to 200 Hz, the second frequency is an average of the first frequency and the third frequency.

4. The physiological signal measuring method according to claim 1, wherein each of the first inputting signal, the second inputting signal and the third inputting signal is an AC electric signal.

5. The physiological signal measuring method according to claim 1, wherein the first inputting signal is a DC electric signal, and each of the second inputting signal and the third inputting signal is an AC electric signal.

6. The physiological signal measuring method according to claim 1, wherein in the step of respectively measuring the first impedance value corresponding to the first inputting signal, the second impedance value corresponding to the second inputting signal and the third impedance value corresponding to the third inputting signal between the electrode sheets and the skin and the step of measuring the skin to obtain the measured physiological signal, the same set of electrode sheets is used.

7. The physiological signal measuring method according to claim 1, wherein the step of respectively measuring the first impedance value corresponding to the first inputting signal, the second impedance value corresponding to the second inputting signal and the third impedance value corresponding to the third inputting signal between the electrode sheets and the skin and the step of measuring the skin to obtain the measured physiological signal are performed separately.

8. The physiological signal measuring method according to claim 1, wherein the step of respectively measuring the first impedance value corresponding to the first inputting signal, the second impedance value corresponding to the second inputting signal and the third impedance value corresponding to the third inputting signal between the electrode sheets and the skin and the step of measuring the skin to obtain the measured physiological signal are performed concurrently.

9. A physiological signal measuring device, comprising:
at least two electrode sheets attached on a skin;
a signal inputting unit for respectively inputting a first inputting signal having a first frequency, a second inputting signal having a second frequency and a third inputting signal having a third frequency to the at least two electrode sheets;
an impedance measuring unit for respectively measuring a first impedance value corresponding to the first inputting signal, a second impedance value corresponding to the second inputting signal and a third impedance value corresponding to the third inputting signal between the at least two electrode sheets and the skin;
a computing unit for obtaining an interference impedance between the at least two electrode sheets and the skin according to the first frequency, the second frequency, the third frequency, the first impedance value, the second impedance value and the third impedance value;
a physiological signal measuring unit for measuring the skin to obtain a measured physiological signal; and
a signal processing unit for correcting the measured physiological signal to obtain a corrected physiological signal according to the interference impedance.

10. The physiological signal measuring device according to claim 9, wherein the first frequency, the second frequency and the third frequency are different from each other.

11. The physiological signal measuring device according to claim 9, wherein the first frequency is smaller than 0.5 Hz, the third frequency ranges from 150 Hz to 200 Hz, and the second frequency is an average of the first frequency and the third frequency.

12. The physiological signal measuring device according to claim 9, wherein each of the first inputting signal, the second inputting signal and the third inputting signal is an AC electric signal.

13. The physiological signal measuring device according to claim 9, wherein the first inputting signal is a DC electric signal, and each of the second inputting signal and the third inputting signal is an AC electric signal.

14. The physiological signal measuring device according to claim 9, wherein the impedance measuring unit and the physiological signal measuring unit share the same set of at least two electrode sheets.

15. The physiological signal measuring device according to claim 9, further comprising:
a switching unit for switching the at least two electrode sheets to be electrically connected to the impedance measuring unit or the physiological signal measuring unit, such that an operation of measuring the first impedance value, the second impedance value and the third impedance value by the impedance measuring unit and an operation of measuring the measured physiological signal by the physiological signal measuring unit are performed separately.

16. The physiological signal measuring device according to claim 9, wherein the impedance measuring unit and the physiological signal measuring unit both are directly connected to the at least two electrode sheets, such that an operation of measuring the first impedance value, the second impedance value and the third impedance value by the impedance measuring unit and an operation of measuring the measured physiological signal by the physiological signal measuring unit are performed concurrently.

* * * * *